(12) United States Patent
Losado et al.

(10) Patent No.: US 8,859,850 B2
(45) Date of Patent: Oct. 14, 2014

(54) POLYNUCLEOTIDE COMPRISING SEQUENCES OF WHEAT GLIADINS AND USE THEREOF FOR SILENCING BY RNAI

(76) Inventors: Francisco Barro Losado, Cordoba (ES); Fernando Pistón Pistón, Cordoba (ES); Javier Gil Humanes, Cordoba (ES); Antonio Martin Munoz, Cordoba (ES)

(*) Notice: Subject to any disclaimer, the term of this patent is extended or adjusted under 35 U.S.C. 154(b) by 241 days.

(21) Appl. No.: 13/147,151

(22) PCT Filed: Jan. 26, 2010

(86) PCT No.: PCT/ES2010/070045
§ 371 (c)(1),
(2), (4) Date: Nov. 25, 2011

(87) PCT Pub. No.: WO2010/089437
PCT Pub. Date: Aug. 12, 2010

(65) Prior Publication Data
US 2012/0167253 A1    Jun. 28, 2012

(30) Foreign Application Priority Data

Feb. 3, 2009   (ES) .................................. 200900302

(51) Int. Cl.
| C12N 15/113 | (2010.01) |
| C12N 15/82  | (2006.01) |
| A01H 5/00   | (2006.01) |
| A01H 5/10   | (2006.01) |

(52) U.S. Cl.
CPC .................................. *C12N 15/8218* (2013.01)
USPC ....... 800/285; 536/24.5; 435/320.1; 435/419; 800/298; 800/320.3

(58) Field of Classification Search
None
See application file for complete search history.

(56) References Cited

U.S. PATENT DOCUMENTS

2005/0260754 A1   11/2005   Kock et al.

FOREIGN PATENT DOCUMENTS

WO   WO2004/078982 A2   9/2004

OTHER PUBLICATIONS

Thomas et al, 2001, Plant J., 25:417-425.*
Folck et al, 2005, Acta Biologica Cracoviensia, 47:33-48, suppl. 1.*
Pistón et al, 2007, Theor. Appl. Genet., 115:77-86.*
Mackintosh et al, 2005, Plant Cell Rep., 25:313-319.*
Becker et al., "Silencing the Alpha Gliadins in Hexaploid Bread Wheat" Gluten Proteins 2006, George L. Lookhart, Perry K. W. Ng, Eds, AACC International, Inc., St. Paul, MN, pp. 86-89, 2006.
Folck et al. "Silencing the α-Gliadins in Wheat" Acta Biologica Cracoviensia. Series Botanica. (Abstracts Oral Presentation XII International Conference on Plant Embryology. Sep. 5-7, 2005, Cracow, Poland)., 47(suppl 1): 40, 2005.
Gil-Humanes et al., "Silencing of Gamma-gliadins by RNA Interference (RNAi) in Bread Wheat", Journal of Cereal Science 48:565-568, 2008.
Gil-Humanes et al., "Effective Shutdown in the Expression of Celiac Disease-related Wheat Gliadin T-cell Epitopes by RNA Interference", Proceedings of the National Academy of Sciences of the United States of America, 107(39):17023-17028, 2010.
Piston et al., "Isolation of Two Storage Protein Promoters from *Hordeum chilense* and Characterization of their Expression Patterns in Transgenic Wheat", Euphytica 162:371-379, 2008.
Rafalski, "Structure of Wheat Gamma-gliadin Genes", Gene 43:221-229, 1986.
Van Herpen, Coeliac Disease Safe Gluten—The Challenge to Reduce Toxicity while Preserving Wheat Technological Properties. PhD thesis, Wageningen University, The Netherlands, ISBN: 978-90-8504-882-4, 2008.
International Search Report, PCT/ES2010/070045, mailed May 17, 2010.
International Preliminary Report on Patentability, PCT/ES2010/070045, mailed Aug. 9, 2011.
Supplementary European Search Report, EP 10 73 8233, dated May 23, 2012.
Examination Report, EP 10 738 233.5, 2012.

\* cited by examiner

*Primary Examiner* — Ashwin Mehta
*Assistant Examiner* — Jason Deveau Rosen
(74) *Attorney, Agent, or Firm* — Occhiuti & Rohlicek LLP

(57) ABSTRACT

The present invention relates to the specific silencing of the α (alpha), β (beta), γ (gamma) and ω (omega)-gliadins of hard wheat for flour by RNA interference (RNAi) through employment of a polynucleotide which is transcribed into an hpRNA (hairpin RNA). Furthermore the present invention additionally relates to a vector, cell, plant or seed comprising the polynucleotide, the expression whereof is specifically directed in particular tissues of wheat seeds through gene expression-regulating sequences such as, for example, the promoter of a gene of γ-gliadins or the promoter of the gene encoding for a D-hordein.

19 Claims, 8 Drawing Sheets

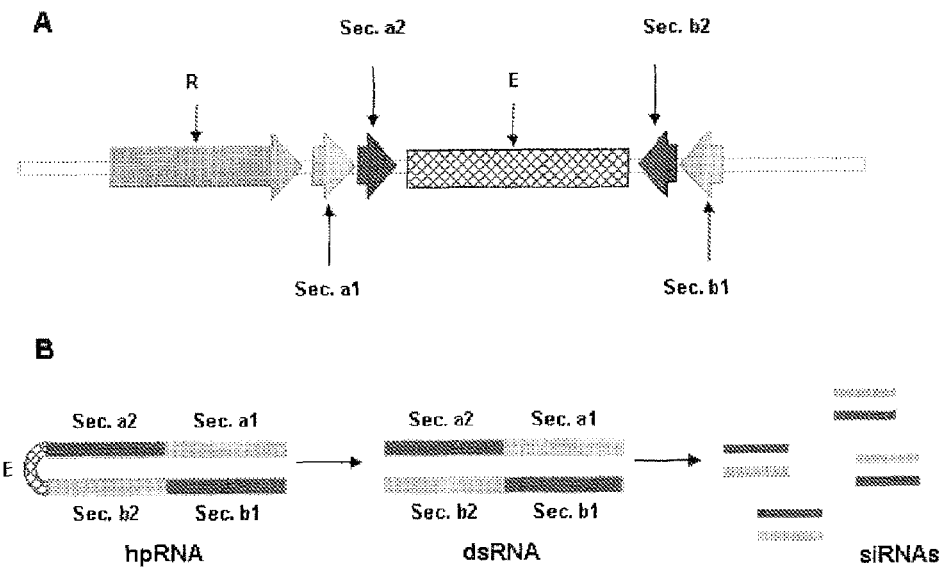
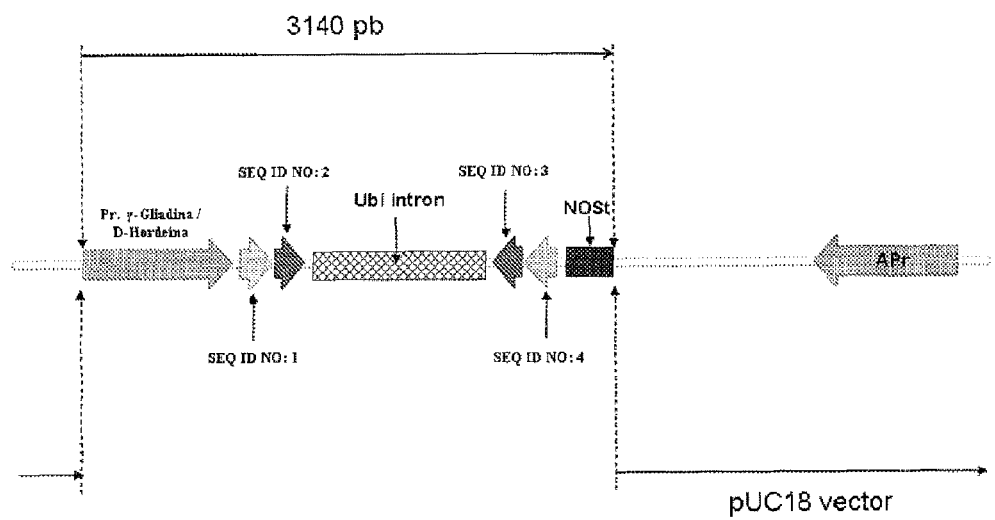
FIG. 1
FIG. 2

SEQUENCE LISTING

<160> NUMBER OF SEQ ID NOS: 17

<210> SEQ ID NO 1
<211> LENGTH: 191
<212> TYPE: DNA
<213> ORGANISM: Artificial Sequence
<220> FEATURE:
<223> OTHER INFORMATION: Description of Artificial Sequence: Synthetic
      sense sequence of omega gliadins

<400> SEQUENCE: 1
ccttcctcat ctttgtcctc cttgccatgg cgatgaagat cgccactgcc gctagggagt      60
taaaccctag caacaaagag ttacaatcac ctcaacaatc attttcccat caacaacaac     120
catttccaca gcagccatat ccacaacaac catatccatc acagcaacca tatccatcgc     180
aacaaccatt t                                                          191

<210> SEQ ID NO 2
<211> LENGTH: 170
<212> TYPE: DNA
<213> ORGANISM: Artificial Sequence
<220> FEATURE:
<223> OTHER INFORMATION: Description of Artificial Sequence: Synthetic
      sense sequence of alpha, beta, gamma gliadins

<400> SEQUENCE: 2

```
caacaacaac tgattccatg cagggatgtt gtattgcaac aacacagcat agcgtatgga      60
agctcacaag ttttgcaaca aagtacttac cagctggtgc aacaattgtg ttgtcagcag     120
ctgtggcaga tccccgagca gtcgcggtgc caggccatcc acaatgttat                170
```

<210> SEQ ID NO 3
<211> LENGTH: 170
<212> TYPE: DNA
<213> ORGANISM: Artificial Sequence
<220> FEATURE:
<223> OTHER INFORMATION: Description of Artificial Sequence: Synthetic
      antisense sequence of alpha, beta, gamma gliadins

<400> SEQUENCE: 3

```
ataacattgt ggatggcctg gcaccgcgac tgctcgggga tctgccacag ctgctgacaa      60
cacaattgtt gcaccagctg gtaagtactt tgttgcaaaa cttgtgagct tccatacgct     120
atgctgtgtt gttgcaatac aacatccctg catggaatca gttgttgttg                170
```

<210> SEQ ID NO 4
<211> LENGTH: 191
<212> TYPE: DNA
<213> ORGANISM: Artificial Sequence
<220> FEATURE:
<223> OTHER INFORMATION: Description of Artificial Sequence: Synthetic
      antisense sequence of omega gliadins

<400> SEQUENCE: 4

```
aaatggttgt tgcgatggat atggttgctg tgatggatat ggttgttgtg gatatggctg      60
ctgtggaaat ggttgttgtt gatgggaaaa tgattgttga ggtgattgta actctttgtt     120
gctagggttt aactccctag cggcagtggc gatcttcatc gccatggcaa ggaggacaaa     180
gatgaggaag g                                                          191
```

<210> SEQ ID NO 5
<211> LENGTH: 1011
<212> TYPE: DNA
<213> ORGANISM: Zea mays

<400> SEQUENCE: 5

```
gttcaaggta cgccgctcgt cctcccccccc cccccctctc taccttctct agatcggcgt      60
tccggtccat ggttagggcc cggtagttct acttctgttc atgtttgtgt tagatccgtg     120
tttgtgttag atccgtgctg ctagcgttcg tacacggatg cgacctgtac gtcagacacg     180
ttctgattgc taacttgcca gtgtttctct tggggaatc ctgggatggc tctagccgtt      240
ccgcagacgg gatcgatttc atgattttt ttgtttcgtt gcatagggtt tggtttgccc     300
ttttccttta tttcaatata tgccgtgcac ttgtttgtcg ggtcatcttt tcatgctttt     360
ttttgtcttg gttgtgatga tgtggtcggg ttgggcggtc gttctagatc ggagtagaat     420
tctgtttcaa actacctggt ggatttatta attttggatc tgtatgtgtg tgccatacat     480
attcatagtt acgaattgaa gatgatggat ggaaatatcg atctaggata ggtatacatg     540
ttgatgcggg tttactgat gcatatacag agatgctttt tgttcgcttg gttgtgatga     600
tgtggtgtgg ttgggcggtc gttcattcgt tctagatcgg agtagaatac tgtttcaaac     660
tacctggtgt atttattaat tttggaactg tatgtgtgtg tcatacatct tcatagttac     720
gagtttaaga tggatggaaa tatcgatcta ggataggtat acatgttgat gtgggttta      780
```

| | |
|---|---|
| ctgatgcata tacatgatgg catatgcagc atctattcat atgctctaac cttgagtacc | 840 |
| tatctattat aataaacaag tatgttttat aattattttg atcttgatat acttggatga | 900 |
| tggcatatgc agcagctata tgtggatttt tttagccctg ccttcatacg ctatttattt | 960 |
| gcttggtact gtttcttttg tcgatgctca ccctgttgtt tggtgttact t | 1011 |

<210> SEQ ID NO 6
<211> LENGTH: 885
<212> TYPE: DNA
<213> ORGANISM: Triticum sp.

<400> SEQUENCE: 6

| | |
|---|---|
| ttccagaaaa aactttgcta atgtatgaca gttatgtagt gaatattttc aacctaagga | 60 |
| acatttttaa tttattttt ataaaattat aattcgactt ggcattcgaa tttggatttg | 120 |
| agttttggtt tgaaacggaa agaggattag taaaatgatt atgatgacat agcatcatta | 180 |
| ggcatgagat tactgtagca tgacatgggg gtgttacact tgtacaatat tcctacccct | 240 |
| gacataaaag gagaatttga tgagtcatgt attgataacg tatacaacat tactaccctt | 300 |
| gacataaaag gagaatttga tgagtcatgc attgataaca tgtacaagat tactatcagc | 360 |
| ttgttcatct taccatcata ttatacaaca ctacaagtta gttttagaaa gaacaagagt | 420 |
| ccacaacaaa tatcagaata cttgcctgat ctatcttaac aacatgcaca aggacacaaa | 480 |
| tttagtcccc cgcaagctat gaagatttgg tttatgtcta acaacttgta cagatccaaa | 540 |
| aggaatgcaa tccagataat tgtttgacat gtaaagtgaa taagatgagt caatgccaat | 600 |
| tatcaagtat tcctcactct tagatgatat gtacaataaa agacaacttt gatgatcac | 660 |
| tctgaaatta cgtttgtatg tagtgccacc aaacacaaca taccaaataa ttagtttgat | 720 |
| aagcatcaaa tcacttttaa aaaagaaagc aataatgaaa agaaacctaa ccatggtagc | 780 |
| yataaaaagg cctacaatat gtagactcca taccatcatc catcgttcac acaactagag | 840 |
| cacaagcaga aaatcaaagt acgtagtagt taacgcaaat ccacc | 885 |

<210> SEQ ID NO 7
<211> LENGTH: 836
<212> TYPE: DNA
<213> ORGANISM: Hordeum chilense

<400> SEQUENCE: 7

| | |
|---|---|
| ccattaattg aactcattcg ggaagcggga aaatttccaa ttctggtata aatcaaacta | 60 |
| tttgacgcga attttctctg aagatcatat gttaattta gacatcactg accaaaggtt | 120 |
| tcagttggtt gagttttgtc acggatacaa gatgcttcca tacgtcaaaa aattctacca | 180 |
| acttttggta cggtgcctcg tagcacggat agatcttgtg tgtcactgga tagatgttgt | 240 |
| gtgtcactag attgatattg tgagtcatag catggatttg tgttgcctgg aaagggaatt | 300 |
| acatgacaag caacaaaacc tgaaatgagc ttttggaaag atgatttatc agtttacttg | 360 |
| ttccatgcaa gctaccttcc actactcgac atgcttagaa gcttcgagtg cccgcggatt | 420 |
| tgccaaagca atggctaaca gacacatatt ctgccaaaaa cccagaacga taatcgcttc | 480 |
| tcgtagatga agagaacaga ccaagataca acgtccaca cttctgcaaa cagtaccccca | 540 |
| gaactaggat taagccgatt acgtggcttt agcagaccgt ccaaaaaaac tgctttgcaa | 600 |
| agctccaatt cctccttgct tatccaattt cttttgtgtt ggcaaactgc acttttccca | 660 |
| accgattctg ttcttcccgt gtttcttctt aggctagcta acatagccgt gcacacagcc | 720 |
| atggtccgga accttcacct cgtccctata aaagcccagc caatctccac aatctcttca | 780 |

```
tcaccgagaa caccgrgcac cacgaaacta gagatcaatt cattgacagt cggatg        836
```

<210> SEQ ID NO 8
<211> LENGTH: 21
<212> TYPE: DNA
<213> ORGANISM: Triticum sp.

<400> SEQUENCE: 8

```
caacaacaac tgattccatg c                                              21
```

<210> SEQ ID NO 9
<211> LENGTH: 20
<212> TYPE: DNA
<213> ORGANISM: Triticum sp.

<400> SEQUENCE: 9

```
ayracattrt ggatggcytg                                                20
```

<210> SEQ ID NO 10
<211> LENGTH: 21
<212> TYPE: DNA
<213> ORGANISM: Triticum sp.

<400> SEQUENCE: 10

```
ccttcctcat ctttgtcctc c                                              21
```

<210> SEQ ID NO 11
<211> LENGTH: 21
<212> TYPE: DNA
<213> ORGANISM: Triticum sp.

<400> SEQUENCE: 11

```
aaatggttgt tgcgatggat a                                              21
```

<210> SEQ ID NO 12
<211> LENGTH: 30
<212> TYPE: DNA
<213> ORGANISM: Triticum sp.

<400> SEQUENCE: 12

```
cagttgttgt tgaaatggtt gttgcgatgg                                     30
```

<210> SEQ ID NO 13
<211> LENGTH: 30
<212> TYPE: DNA
<213> ORGANISM: Triticum sp.

<400> SEQUENCE: 13

```
caacaaccat ttcaacaaca actgattcca                                     30
```

<210> SEQ ID NO 14
<211> LENGTH: 23
<212> TYPE: DNA
<213> ORGANISM: Triticum sp.

<400> SEQUENCE: 14

```
ttccagaaaa aactttgcta atg                                            23
```

<210> SEQ ID NO 15
<211> LENGTH: 20
<212> TYPE: DNA
<213> ORGANISM: Hordeum chilense

```
<400> SEQUENCE: 15
ccattaattg aactcattcg                                                    20

<210> SEQ ID NO 16
<211> LENGTH: 19
<212> TYPE: DNA
<213> ORGANISM: Streptomyces hygroscopicus

<400> SEQUENCE: 16
gtctgcacca tcgtcaacc                                                     19

<210> SEQ ID NO 17
<211> LENGTH: 20
<212> TYPE: DNA
<213> ORGANISM: Streptomyces hygroscopicus

<400> SEQUENCE: 17
gaagtccagc tgccagaaac                                                    20
```

POLYNUCLEOTIDE COMPRISING SEQUENCES OF WHEAT GLIADINS AND USE THEREOF FOR SILENCING BY RNAI

CROSS-REFERENCE TO RELATED APPLICATIONS

This application is a U.S. national phase application filed under 35 U.S.C. §371 of International Application No. PCT/ES2010/070045, which was filed Jan. 26, 2010, and which claims the benefit of the priority date of Spanish Application No. P200900302 filed Feb. 3, 2009. For the purpose of any U.S. patent that may issue from the U.S. national phase application, the content of the priority documents is hereby incorporated by reference in its entirety.

SEQUENCE LISTING

The instant application contains a Sequence Listing which has been submitted in ASCII format via EFS-Web and is hereby incorporated by reference in its entirety. Said ASCII copy, created on Mar. 5, 2012, is named U2149301.txt and is 7,411 bytes in size.

The present invention concerns the specific silencing of the α (alpha), β (beta), γ (gamma), and ω (omega) gliadins of hard wheat and flour by interference RNA (iRNA) through use of a polynucleotide that is transcribed into an hpRNA (hairpin RNA). Furthermore, the present invention also concerns a vector, cell, plant, or seed comprising the polynucleotide, the expression whereof is specifically directed in particular tissues of wheat seeds through gene expression-regulating sequences such as, for example, the promoter of a gene of γ gliadins or the promoter of the gene that codes for a D-hordein.

PRIOR ART

RNA interference (RNAi) is a system of degradation of messenger RNA mediated by double-stranded RNA that allows the specific silencing of particular genes. Its discovery has made it possible to design vectors composed of a promoter and termination signals including the sequence of the gene one wishes to silence and having sense and antisense sequences separated by a spacer sequence of variable length.

siRNAs (the English abbreviation for small interfering RNA or short interfering RNA) are molecules of double-stranded RNA (dsRNA, the English abbreviation for double-stranded RNA) of 21-25 nucleotides (nt) that originate from a longer precursor dsRNA. Precursor dsRNAs may be of endogenous origin, in which case they are referred to as miRNAs (encoded in the genome of the organism) or of exogenous origin (such as viruses or transgenes). Both siRNA and miRNA are types of iRNA (interference RNA). iRNA suppresses the post-transcriptional expression of a particular mRNA (the English abbreviation for messenger RNA) recognized by the iRNA sequence.

When a cell receives a dsRNA precursor (single-stranded RNAs do not produce this effect), which may be generated from an exogenous transgene, a viral agent, or an endogenous genetic element, it is fragmented into siRNAs through the action of an enzyme referred to as Dicer, a cytoplasmic enzyme of the RNAse III family. Dicer cleaves the dsRNA into double-stranded fragments of approximately 21-25 nucleotides (siRNA), with the 5' end phosphorylated and two unpaired nucleotides protruding at the 3' end. Of the two strands of siRNA, only one, referred to as the guide strand, is incorporated into the enzymatic complex RISC (RNA-induced silencing complex), while the other strand is degraded. The thermodynamic characteristics of the 5' end of the siRNA determine which of the two strands is incorporated into the RISC complex. The strand that is less stable at the 5' end is normally incorporated as the guide strand, either because it has a higher content of AU bases or because of imperfect pairings. The guide strand must be complementary to the mRNA to be silenced in order for post-transcriptional silencing to occur. Subsequently, the RISC complex binds to the complementary mRNA of the guide strand of the siRNA present in the complex, and cleavage of the mRNA occurs. After this, the fragments obtained are degraded. In this manner, the siRNAs cause post-transcriptional silencing of the target nucleotide sequences so that the protein that would result from expression of these sequences is not obtained.

The grain proteins in wheat, although contained in lesser amounts (7-18%) than carbohydrates (60-75%), are essential for the functional properties of flour. The main grain proteins are the glutenins and gliadins, which make up gluten. The gliadins have been found to be responsible for the development of celiac disease, as epitopes (antigenic determinants) recognized by the intestinal T cells have been identified in regions of α and γ gliadins (Arentz-Hansen, et al., 2002. *Gastroenterology* 123: 803-809). People suffering from celiac disease are intolerant to gluten. Gluten intolerance is characterized by chronic inflammation of the proximal portion of the small intestine caused by exposure to gliadin. By producing wheat having a sharply reduced gliadin content, it would be possible to produce a food for celiac disease patients.

There are four known types of gliadins: α (alpha), β (beta), γ (gamma), and ω (omega). Suppression of wheat grain gliadins using RNAi technology has been used in recent years. To date, it has only been possible to suppress particular gliadins. For example, by using genetic constructions that give rise to an RNAi type hairpin having the structure promoter-sense sequence-spacer-antisense sequence-terminator, it has been possible to eliminate type α gliadins (Folck et al., 2005. XII International Conference on Plant Embryology. Oral presentation) or γ type gliadins (Gil-Humanes et al. 2008. *Journal of Cereal Science* 48(3): 565-568) almost completely, but it has not yet been possible to effectively eliminate all types of gliadins.

Obtaining plants having seeds with a highly reduced gliadin content presents technical difficulties, e.g., first, the increased number of genes coding for gliadins, and second, the fact that wheat plants are hexaploid. There are more difficulties involved in achieving stable transformation in wheat plants than in transformation of any other plant having fewer copies of the genome.

EXPLANATION OF THE INVENTION

The present invention concerns a polynucleotide comprising two sequence pairs, with each subsequence combining in a particular order to give rise to a sequence whose transcription into RNA is capable of generating hpRNA (hairpin RNA), e.g., RNA in the shape of a hairpin, a double-stranded RNA that will be processed by endoribonucleases described in the prior art, which is used to generate the siRNAs that cause post-transcriptional silencing of all of the mRNAs (messenger RNA) that code for all types of wheat gliadins. For this purpose, the four subsequences are: the sense sequence of the ω gliadins, the sense sequence of the α, β, and γ gliadins, and the two previous antisense sequences.

By means of this polynucleotide, whose expression is specifically directed in particular to tissues of wheat seeds through gene expression-regulating sequences such as, for example, the promoter of a gene of γ gliadins or the promoter of the gene that codes for a D-hordein, one achieves post-transcriptional silencing of all of the genes of the species soft wheat and hard wheat in an effective and synergistic manner, as one is able to silence a greater number of gliadin genes compared to the results of silencing of α and γ gliadins by hpRNA described in the prior art. This is essentially due to the specific design of the sense and antisense subsequences whose generated siRNA hybridizes with all of the mRNA of the α, β, γ, and ω gliadins of wheat in combination with gliadin promoters having higher levels of expression that can be induced in specific tissues of the wheat seed. This design was arrived at by identifying groups of gliadins containing epitopes recognized by human T cells, such that silencing of the proteins containing them gives rise to wheat seeds that can be used to obtain products suitable for persons allergic to gluten.

In the present invention, the terms DNA and RNA are used to refer to deoxyribonucleic acid and ribonucleic acid respectively.

Therefore, one aspect of the present invention is a polynucleotide that is at least 90% identical to a sequence comprising two sequence pairs (a1-a2) and (b2-b1) separated by a spacer sequence in which:
a. the sequences a1, a2, b1, and b2 differ among themselves and are selected from SEQ ID NO: 1, SEQ ID NO: 2, SEQ ID NO: 3, or SEQ ID NO: 4, in the following form:
b. if a1 is SEQ ID NO: 1 or SEQ ID NO: 4, b1 is SEQ ID NO: 4 or SEQ ID NO: 1, and a2 is SEQ ID NO: 2 or SEQ ID NO: 3, and
c. if a1 is SEQ ID NO: 2 or SEQ ID NO: 3, b1 is SEQ ID NO: 3 or SEQ ID NO: 2, and a2 is SEQ ID NO: 1 or SEQ ID NO: 4.

Another aspect of the present invention is a polynucleotide that comprises two sequence pairs (a1-a2) and (b2-b1) separated by a spacer sequence in which the sequences a1, a2, b1, and b2 are described in paragraphs (a) through (c) of the previous aspect.

The sequences a1-a2 and b2-b1 (referred to in the following as the sequence pairs of the invention) are linked to form a linear and continuous nucleotide sequence in which, in turn, the two pairs are linked among themselves by means of a spacer sequence at least one nucleotide in length. Preferably, the spacer sequence is a non-coding sequence that is eliminated after the process of forming dsRNA. The spacer sequence may be part of a sequence of an intron of a gene. The function of the spacer sequence is to act as a hinge for the sequence pairs described so that pairing or hybridization of the RNA sequences coding for the polynucleotide may take place.

The polynucleotide is at least 90% identical with the sequence that comprises the sequence pairs of the invention. In this manner one takes into account changes in any of the nucleotides that make up the sequence pairs, up to a percentage of 90% identity with the original sequence whose nucleotide composition is specified in the present aspect.

SEQ ID NO: 1 is the sense sequence that comprises a part of the fragment that codes for the epitopes of ω gliadins recognized by human T cells that give rise to an immune response in persons suffering from celiac disease. SEQ ID NO: 2 is the sense sequence that comprises a part of the fragment that codes for the epitopes of α, β, and γ gliadins. SEQ ID NO: 3 is the antisense sequence of SEQ ID NO: 2, and SEQ ID NO: 4 is the antisense sequence of SEQ ID NO: 1.

The polynucleotide of the invention gives rise to RNA in which the two sequence pairs hybridize with each other, forming a hairpin. Therefore, according to these first two aspects of the present invention, the combinations of sequences by means of which RNA hairpins can be obtained are shown in Table 1 and Table 2:

TABLE 1

Combinations of sequences in which the a1-a2 and b2-b1 pairs are sense or antisense sequences.

| Combinations | a1 | a2 | b2 | b1 |
|---|---|---|---|---|
| 1 | SEQ ID NO: 1 | SEQ ID NO: 2 | SEQ ID NO: 3 | SEQ ID NO: 4 |
| 2 | SEQ ID NO: 2 | SEQ ID NO: 1 | SEQ ID NO: 4 | SEQ ID NO: 3 |
| 3 | SEQ ID NO: 3 | SEQ ID NO: 4 | SEQ ID NO: 1 | SEQ ID NO: 2 |
| 4 | SEQ ID NO: 4 | SEQ ID NO: 3 | SEQ ID NO: 2 | SEQ ID NO: 1 |

TABLE 2

Combinations of sequences in which the a1-a2 and b2-b1 pairs contain sense and antisense sequences.

| Combinations | a1 | a2 | b2 | b1 |
|---|---|---|---|---|
| 1 | SEQ ID NO: 1 | SEQ ID NO: 3 | SEQ ID NO: 2 | SEQ ID NO: 4 |
| 2 | SEQ ID NO: 3 | SEQ ID NO: 1 | SEQ ID NO: 4 | SEQ ID NO: 2 |
| 3 | SEQ ID NO: 2 | SEQ ID NO: 4 | SEQ ID NO: 1 | SEQ ID NO: 3 |
| 4 | SEQ ID NO: 4 | SEQ ID NO: 2 | SEQ ID NO: 3 | SEQ ID NO: 1 |

In a preferred embodiment of the present invention, the polynucleotide comprises two sequence pairs (a1-a2) and (b2-b1) separated by a spacer sequence in which a1 is SEQ ID NO: 1, a2 is SEQ ID NO: 2, b2 is SEQ ID NO: 3, and b1 is SEQ ID NO: 4.

According to another preferred embodiment, the polynucleotide comprises two sequence pairs (a1-a2) and (b2-b1) in which the spacer sequence is SEQ ID NO: 5. The sequence SEQ ID NO: 5 is a fragment of an intron of the gene Ubi1 that codes for maize ubiquitin. An intron is a region of DNA that is eliminated from the primary RNA transcript by a process referred to as splicing, i.e., the intron does not code for any sequence of a protein. Ubiquitin is a protein that has the function of marking other proteins for destruction.

Another preferred embodiment is a polynucleotide that also comprises a gene expression-regulating sequence functionally linked to its 5' end. In the present invention, the term gene expression-regulating sequence refers to a nucleic acid sequence that affects the functionality of the gene with respect to the beginning of transcription of a DNA sequence or the beginning of translation of an RNA sequence or other undescribed sequences. By way of example, the gene expression-regulating sequences covered by the present invention are promoters and other less common sequences such as certain introns. The regulatory sequence binds to the 5' end of the polynucleotide of the present invention in a functional manner, i.e., it is capable of directing the expression of the polynucleotide with an intensity and localization that depend on its own regulatory sequence.

According to a more preferable embodiment, the gene expression-regulating sequence is SEQ ID NO: 6 and/or SEQ ID NO: 7. The sequence SEQ ID NO: 6 corresponds to the sequence of a promoter of the γ gliadin gene that shows a duplication in a proline box. SEQ ID NO: 7 corresponds to the sequence of a promoter of the D-hordein gene (the second nucleotide of this gene has the accession number AY998009 and belongs to the species *Hordeum chilense*). Both promoters are expressed in the endosperm of the seeds.

Also included are the sequences that are complementary to any of the polynucleotides of the present invention.

In the following, the terms "polynucleotides of the invention" or "polynucleotides of the present invention" will be used to refer to any of the above polynucleotides.

Another aspect of the present invention is an RNA sequence coded for by any of the polynucleotides of the invention and capable of forming an hpRNA in which the sequence coded for by the pair a1-a2 hybridizes completely with the sequence coded for by the pair b2-b1.

An hpRNA (the English abbreviation for hairpin RNA) is a hairpin shape formed by hybridization of the transcribed sequences. In the present invention, the polynucleotide of the present invention in which the sequence pairs a1-a2 and b2-b1 completely hybridize between themselves was used as a template for synthesizing the transcribed sequences, as can be seen in FIG. 1B. An hpRNA is a double-stranded RNA (dsRNA) that is cleaved by an endoribonuclease, for example the endoribonuclease Dicer, resulting in fragments of approximately 21-25 nts. These fragments are known as siRNA. As has been described above, the siRNAs cause post-transcriptional silencing of the target nucleotide sequences so that the protein that would result from the expression of mRNA sequences is not obtained.

Another aspect of the present invention is at least one siRNA generated from the sequence of the hpRNA according to the previous aspect. The siRNA can also be referred to as RNAi. The siRNA is a double-stranded RNA of between 21 and 25 nucleotides, but is not limited to this number of nucleotides, and it is generated from the hpRNA sequence of the invention. In the present invention, in defining the approximate number of nucleotides of the siRNA (approximately 21 and 25 nucleotides), it is understood that there is another strand that is complementary to this sequence, i.e., that one can use the terms nucleotides or base pairs (bp) interchangeably.

As has been described, the Dicer enzyme cleaves the dsRNA into double-stranded fragments of approximately 21-25 nucleotides (siRNA), with the 5' end phosphorylated and two unpaired nucleotides protruding at the 3' end. Of the two strands of siRNA, only one, referred to as the guide strand, is incorporated into the enzymatic complex RISC, while the other is degraded. The thermodynamic characteristics of the 5' end of the siRNA determine which of the two strands is incorporated into the RISC complex. The strand that is less stable at the 5' end is normally incorporated as the guide strand. The guide strand must be complementary to the mRNA that is to be silenced in order for post-transcriptional silencing to occur. Subsequently, the RISC complex binds to the complementary mRNA of the guide strand of the siRNA present in the complex, and cleavage of the mRNA occurs.

Another aspect of the present invention is an expression vector that comprises any of the polynucleotides of the invention. In the following, "vector of the invention" or "vector of the present invention."

The term "vector" refers to a DNA fragment that has the capacity to replicate itself in a particular host, and, as the term indicates, may serve as a vehicle for multiplying another DNA fragment that has been fused to it (an insert). "Insert" refers to a DNA fragment that is fused to the vector; in the case of the present invention, the vector comprises the polynucleotide of the invention, which, when fused thereto, can replicate itself in the corresponding host. Vectors may be plasmids, cosmids, bacteriophages, or viral vectors, without excluding other types of vectors that meet the present definition of vector.

Another aspect of the present invention is an isolated cell transfected with the vector of the invention. In the following, "cell of the invention" or "cell of the present invention." The term "cell" as used in the present invention refers to a prokaryotic or eukaryotic cell. The cell may be a bacterium capable of replicating foreign DNA by transforming, for example, any of the strains of the species *Escherichia coli* or a bacterium capable of transferring the DNA of interest into the interior of a plant, such as for example *Agrobacterium tumefaciens*. Preferably, the cell refers to a eukaryotic plant cell, and within this group, more preferably to cells belonging to the kingdom Plantae. Therefore, in cases in which the cell is a plant cell, the term "cell" comprises at least a parenchyma cell, meristem cell, or a cell of any type, differentiated or undifferentiated. Thus, this definition also includes a protoplast (a plant cell lacking a cell wall).

The term "transfection" refers to the introduction of external genetic material into cells via plasmids, viral vectors (in this case one can also use the term "transduction"), or other means of transfer. The term "transfection by nonviral methods" is used with reference to mammalian eukaryotic cells, while the term "transformation" is preferred to describe nonviral transfers of genetic material into bacteria and non-animal eukaryotic cells such as yeasts, algae, and plants. In the case of the present invention, the term "transfection" is equivalent to the term "transformation."

Another aspect of the present invention is a genetically modified plant that comprises the cell of the invention. The term "plant" includes every part of the plant, which may be preserved or cultivated either individually or in combination, as well as the germplasm. The germplasm is composed of biological material that contains interspecies genetic variability or the genetic materials that can perpetuate a species or population of an organism (see seeds, propagule, or progeny below). The plant must comprise the cell of the present invention in a form that is expressed in a specific tissue (at a specific moment of plant development or depending on the environmental conditions in which it develops) or in a constitutive or epitopic form (expressed in other cells or tissues differing from those that are common and expected).

The plant of the invention may contain the polynucleotide of the invention in homozygosis, heterozygosis, or hemizygosis.

According to a preferred embodiment, the plant belongs to the genus *Triticum*. The plant is selected from the list that includes, but is not limited to, *Triticum aestivum, T. aethiopicum, T. araraticum, T. boeoticum, T. carthlicum, T. compactum, T. dicoccoides, T. dicoccum, T. durum, T. ispahanicum, T. karamyschevii, T. macha, T. militinae, T. monococcum, T. polonicum, T. repens, T. spelta, T. sphaerococcum, T. timopheevii, T. turanicum, T. turgidum, T. urartu, T. vavilovii* and *T. zhukovskyi*.

According to another preferred embodiment, the plant is of the species *Triticum aestivum* or *Triticum turgidum*. According to another preferred embodiment, the plant belongs to the cultivar Bobwhite or the cultivar Don Pedro. More preferably, the cultivars BW208 and BW2003 (Bobwhite), which belong to the wheat species *Triticum aestivum* L. ssp *aestivum*, and the variety Don Pedro, which belongs to the wheat species *Triticum turgidum* L. ssp *durum*, are selected.

Bobwhite is the name of the cultivar obtained from the International Maize and Wheat Improvement Center (CIMMYT). BW208 and BW2003 are different Bobwhite lines.

Don Pedro is a hard wheat variety, also from CIMMYT. Bobwhite and Don Pedro are public varieties.

The plant of the invention may be obtained by genetic transformation of plant cells by means of biolistics, *Agrobacterium tumefaciens*, or any other technique that allows integration of the polynucleotide of the invention into the DNA of the plant, whether this DNA be genomic, chloroplastic, or mitochondrial, followed, although not necessarily, by an in vitro regeneration program suited to the characteristics and requirements of the transformed plant species. Moreover, the plant may also be obtained by transference of any of the sequences of the invention by crossing, e.g., using pollen of the plant of the invention to pollinate any other plant that does not contain the polynucleotide of the invention, or pollinating the gynoecia of plants containing the polynucleotide of the invention with other pollen that does not contain these sequences. The methods for obtaining the plant of the invention are not exclusively limited to those described in this paragraph; for example, genetic transformation of germ cells from the ear of wheat could be carried out as mentioned, but without having to regenerate a plant afterward (see below). Moreover, a plant that comprises the cell of the present invention in a stable or transient form is also included.

Another aspect of the present invention is a seed from any of the plants of the invention. This will be referred to below as the "seed of the invention" or "seed of the present invention".

Another aspect of the present invention is a grain of pollen, propagule, progeny, or plant part derived from any of the plants of the invention.

In the present invention, pollen is taken into account as a transmitter of the genetic and phenotypic characteristics that may result from pollination of any plant variety compatible with the pollen in question. In this manner, one obtains a plant that comprises the polynucleotide of the present invention, and, after the respective crosses and/or selections, one can obtain a plant in which the sequence is integrated in stable form (although it may also be expressed in transient form) and in a sufficient number of copies to obtain the same desirable characteristics in subsequent generations.

Propagules are parts of the plant that allow asexual propagation or reproduction in plants, whereby new individualized plants or organs are obtained. The tissues of the separated portion must recover to the status of meristems in order to produce the entire group of organs of the plant. The propagule is selected from the list that comprises, without being exhaustive, stolons, rhizomes, tubers, or bulbs.

The term "progeny" refers to the result of reproduction, i.e., the individual or individuals produced by the intervention of one or more parent individuals. For example, the progeny of plants obtained by sexual reproduction are seeds, but the progeny of a plant may be any cell resulting form the fusion of any cellular contents, plastid, cellular compartment, DNA, or any combinations thereof. In the processes of cellular division (such as in vitro cultivation, for example), the progeny are the cells resulting from the division.

Another aspect of the present invention is the use of the polynucleotide, vector, or cell of the invention for the silencing of alpha, beta, gamma, and omega gliadins of *Triticum* spp.

As shown in Example 2 of the present invention, the integration of the polynucleotide of the invention into the genome of wheat plants of two genotypes of wheat for flour (*Triticum aestivum* L.), cultivar Bobwhite (BW208 and BW2003), and one of hard wheat (*Triticum turgidum* ssp *durum*), cultivar Don Pedro, causes silencing of the alpha, beta, gamma, and omega gliadins of the seeds of transformant plants (FIG. 3, FIG. 4, and FIG. 5).

Another aspect of the present invention is the use of the seed of the invention to prepare a food composition (referred to in the following as the "composition of the invention" or "composition of the present invention"). The food composition is prepared from, but not limited to, the flour and/or semolina of the seeds of the invention, combined or not with other flours and/or semolinas, or other compounds.

The term "flour" as it is understood in the present invention refers to the product obtained by milling of any seed or plants of the genus *Triticum*, with the bran or husk of the seed removed to a greater or lesser degree.

The term "semolina" refers to coarse flour (slightly milled wheat seeds), i.e., fragments of the endosperm with a variable amount of seed husks.

The prepared food is selected from, but not limited to, the list comprising bread, bakery products, pastries, confectionery products, food pasta, food dough, grains, drinks, or dairy products.

Another aspect of the invention is use of the composition of the invention to prepare a functional food product, vitamin supplement, or nutritional supplement. As understood in the present invention, a food product fulfills a specific function, such as improving the diet of those who consume it. For this purpose, a vitamin and/or nutritional supplement may be added to the functional food product.

The food product that comprises the food composition of the present invention may be eaten even by persons who are allergic to gluten, i.e., suffer from celiac disease.

Another aspect of the present invention is a method for obtaining the plant of the invention, comprising the following:

a. selecting a part of the plant,
b. transfecting the cells of the part of the plant of paragraph (a) with a vector according to claim 9,
c. selecting the transfected cell of paragraph (b) that comprises the polynucleotide according to any of claims 1 through 6,
d. regenerating at least one plant derived from the cell selected in paragraph (c),
e. selecting one or more plants regenerated according to paragraph (d) in which the polynucleotide is transcribed into an hpRNA, and
f. selecting one or more plants obtained according to paragraph (e) that show silencing of the alpha, beta, gamma, and omega gliadins in its seeds.

In the case of wheat plants, one should preferably select the scutellum to be transfected by the vector of the invention. The insertion of the polynucleotide of the present invention into a vector may be carried out by cloning methods that are known in the art, by means of cleaving the polynucleotide and the vector with restriction enzymes (digestion) and subsequent ligation, such that the sequence of the vector comprises the polynucleotide of the invention. The vector was described in a previous paragraph.

The selection of the vector that comprises the selected sequence of the invention may be carried out by techniques such as the following:

Selection of cells containing the vectors of the invention by means of adding antibiotics to the culture medium. The resistance of these cells to substances such as antibiotics is produced by the synthesis of molecules coded for by a sequence contained in the sequence of the vector.

Digestion with restriction enzymes, by means of which one obtains a fragment of one of the sequences of the invention inserted into the vector.

The cell is obtained by any type of microbiological culture (for example, *E. coli* or *Agrobacterium tumefaciens*) or plant culture.

Genetic transformation of the cells is carried out using techniques known in the art, such as, for example, electroporation, genetic transformation by biolistics, *Agrobacterium tumefaciens*, or any other technique that allows the integration of any of the sequences of the invention into the DNA of the cell. Preferably, transformation should be carried out by biolistics. By means of these techniques, one can obtain in a stable manner a vector that comprises any of the sequences of the invention, such that after successive cell divisions, the incorporated sequence continues to express itself. Cells including any of the sequences of the invention in a transient manner are also included.

The cell transformed with a vector that comprises any of the polynucleotides of the invention may incorporate the sequence in any type of cellular DNA: nuclear, mitochondrial, and/or chloroplastic, and in this case, one usually inserts the DNA, which comprises, among other sequences, the polynucleotide of the invention. Selection of cells that have incorporated any of the sequences of the invention is carried out by adding antibiotics to the culture medium that provides nutrients to them. The resistance of these cells to substances such as antibiotics or herbicides is produced by the synthesis of molecules coded for by a sequence contained in the DNA sequence of the vector. One may also select the cell that comprises the polynucleotide of the invention by any other technique that allows its presence or absence and/or its expression to be distinguished.

The plant cells selected may be subjected to a program of organogenesis or somatic embryogenesis, thus giving rise to a complete plant that comprises the genetic material of the original cell from which it originated. This is possible because of the fact that plant cells are totipotent, i.e., by means of a suitable combination of hormones, they can be dedifferentiated, thus generating embryonic cells that, because they contain a complete copy of the genetic material of the plant to which they belong, have the potential to regenerate a complete new plant. Light and temperature conditions suited to each plant species are also required. Once the plant originating from the selected plant cell has regenerated itself, one can carry out an analysis of the presence and/or expression of the nucleotide sequence that codes for the polynucleotide of the invention or any other sequence of the present invention (promoter sequence, etc.)

The method also includes the selection of a plant that shows substantial silencing of the alpha, beta, gamma, and omega gliadins in its seeds. Preferably, plants showing virtually complete or complete silencing of all the gliadins of the seeds should be selected. The reduction in total gliadin content of a control plant (a plant not including the polynucleotide of the invention) is greater than or equal to 90%. The control plants preferably do not contain the polynucleotide of the invention in the plant cell. Prior to being transformed, the control may also be a wild-type plant that has undergone the same in vitro cultivation steps as the plants of the invention or has not undergone these cultivation steps.

The transfected cells may be germ cells from the ear of the plant, and in this case, at least one plant derived from the seeds generated by said ear of the plant would be regenerated, and one would select at least one plant showing silencing of the alpha, beta, gamma, and omega gliadins in its seeds.

Throughout the description and the claims, the word "comprise" and its variants is not intended to exclude other technical characteristics, additives, components, or steps. For the person skilled in the art, other objects, advantages, and characteristics of the invention will be obvious partly from the description and partly from the practice of the invention. The following figures and examples are provided by way of illustration, and they are not intended to limit the scope of the present invention.

DESCRIPTION OF THE FIGURES

FIG. 1. Shows the structure of the polynucleotide of the invention.

Figure A shows a polynucleotide that comprises the sequence pairs a1-a2 and b2-b1, separated by a spacer sequence (E) whose expression is directed by a gene expression-regulating sequence (R).

Figure B shows the hpRNA resulting from transcription of the polynucleotide represented in Figure A in which is formed a hairpin, in which the sequences Sec a1, a2, b2, and b1 hybridize as is described. Subsequently, this RNA is processed, producing a new sequence of double-stranded RNA (dsRNA). The final step shown refers to fractionation of the prior sequence by enzymes such as, for example, the enzyme Dicer, such that double-stranded RNA sequences of approximately 21-25 nucleotides, referred to as siRNA (small interfering RNA), are formed.

FIG. 2. Shows a specific example of the polynucleotide of the invention.

In this case, the sequence R is a promoter sequence of the gene of gamma-gliadin (γ gliadin) or D-hordein. Sequence E is a fragment of an intron of the maize ubiquitin gene. NOSt is a transcription termination sequence. This polynucleotide is inserted in this specific example into a pUC18 vector that has an ampicillin resistance gene.

Figure 3:
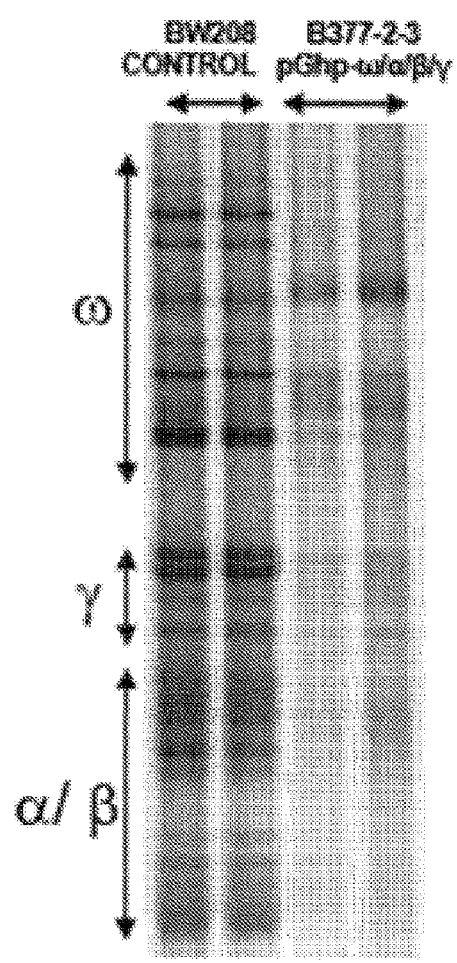
Figure 3:
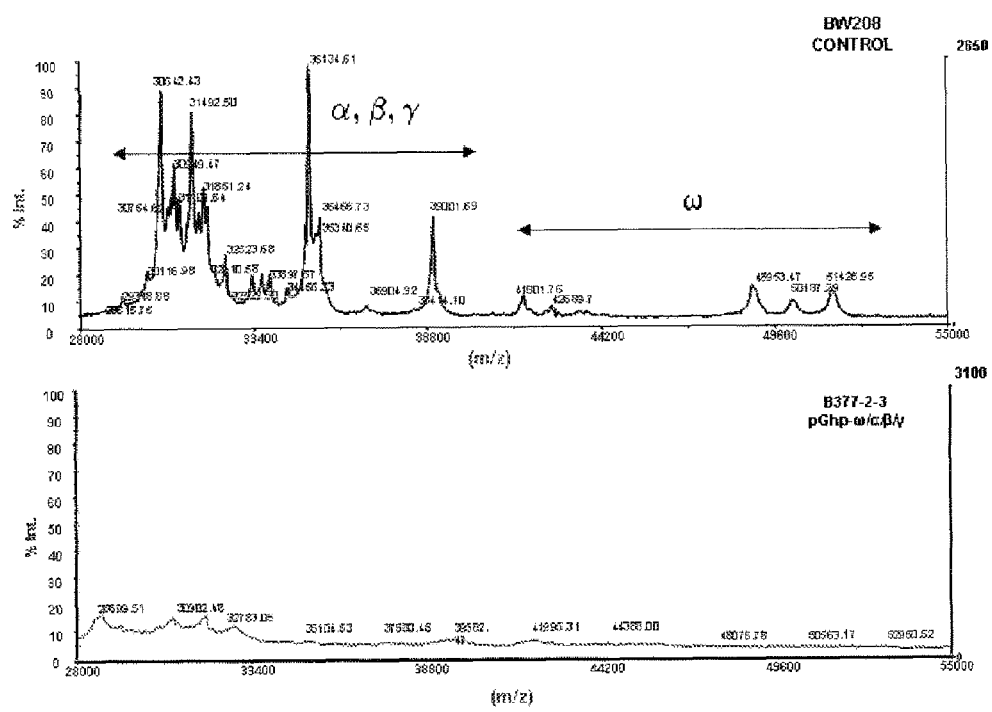

FIG. 3. Shows separation and identification of gliadins of plant seeds of the wheat variety BW208, transformed with the polynucleotide of the invention, by the A-PAGE and MALDI-TOF techniques.

Figure A shows separation by A-PAGE of the gliadins of the sample of seeds of a control line of wheat for flour (*Triticum aestivum* L. ssp. *aestivum*), variety BW208, and a line of wheat for flour of the same genotype transformed with the vector pGhp-ω/α/β/γ (B377-2-3). The groups of gliadins obtained by separation are indicated.

Figure B shows a MALDI-TOF analysis of gliadins from a sample of a control line of seeds from wheat for flour (*Triticum aestivum* L. ssp. *aestivum*), variety BW208, and a line of wheat for flour of the same genotype transformed with the vector pGhp-ω/α/β/γ. In the diagram corresponding to the control line, the various fractions of alpha (α), beta (β), gamma (γ), and omega (ω)-gliadins are indicated. The X axis represents the ratio (m/z) of the mass of given ion (m) and the number of protons it contains (z).

Figure 4:
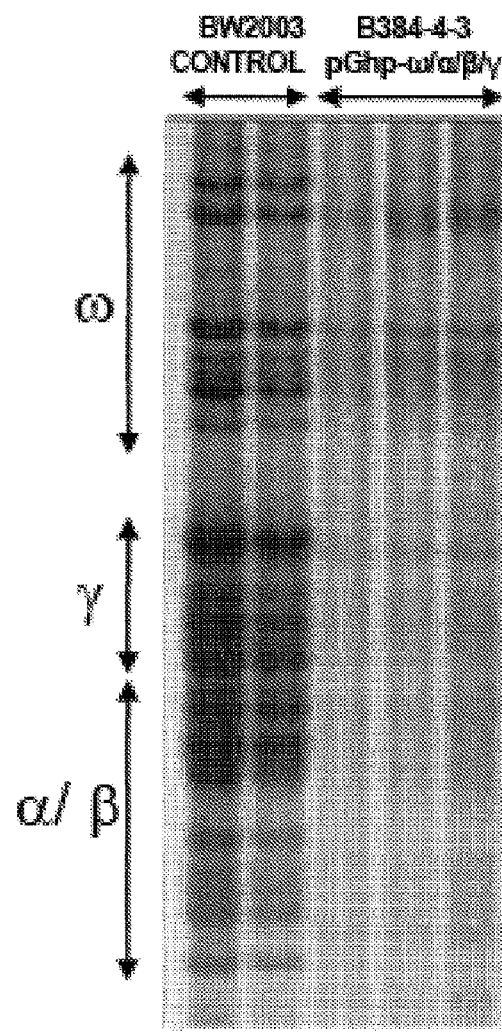

FIG. 4. Shows separation and identification by A-PAGE of the gliadins of plant seeds of the wheat variety BW2003 transformed with the polynucleotide of the invention.

A-PAGE gel separation of gliadins from a control line of wheat for flour (*Triticum aestivum* L. ssp. *aestivum*), variety BW208, and a line of wheat for flour of the same genotype transformed with the vector pGhp-ω/α/β/γ. The groups of gliadins obtained in the separation are indicated.

Figure 5:
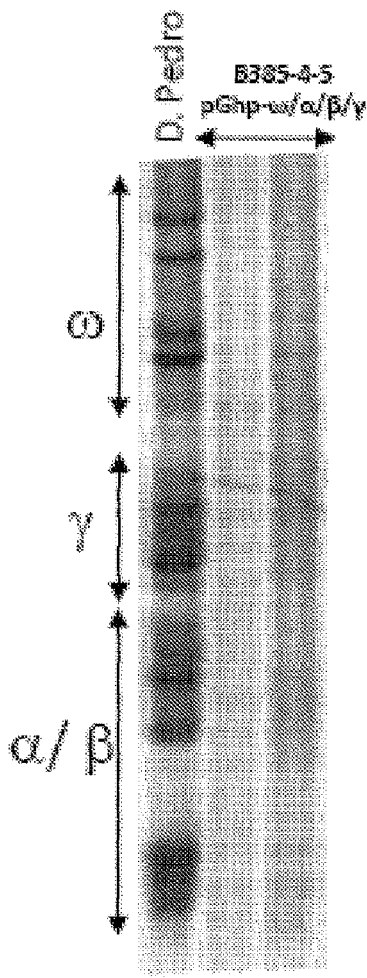

FIG. 5. Shows separation and identification by the A-PAGE technique of gliadins of seeds from plants of the hard wheat variety Don Pedro transformed with the polynucleotide of the invention.

A-PAGE gel separation of gliadins of a control line of hard wheat (*Triticum turgidum* L. ssp. *durum*), variety Don Pedro, and a line of hard wheat of the same genotype transformed with the vector pGhp-ω/α/β/γ. The groups of gliadins obtained in the separation are indicated.

Figure 6:
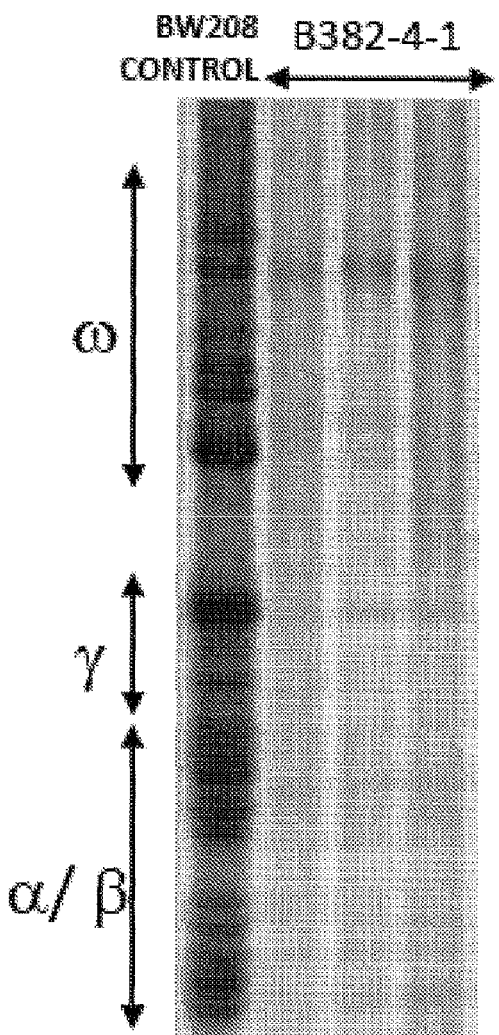

FIG. 6. Shows separation and identification by the A-PAGE technique of gliadins of seeds from plants of the variety BW208 transformed with the polynucleotide of the invention.

A-PAGE gel separation of gliadins of a control line BW208 and three seeds of a line (B382-4-1) of the same genotype transformed with the vector pDhp-ω/α/β/γ. The groups of gliadins obtained by separation are indicated. Note that the promoter that comprises this vector is a D-hordein promoter (SEQ ID NO: 7).

Figure 7:
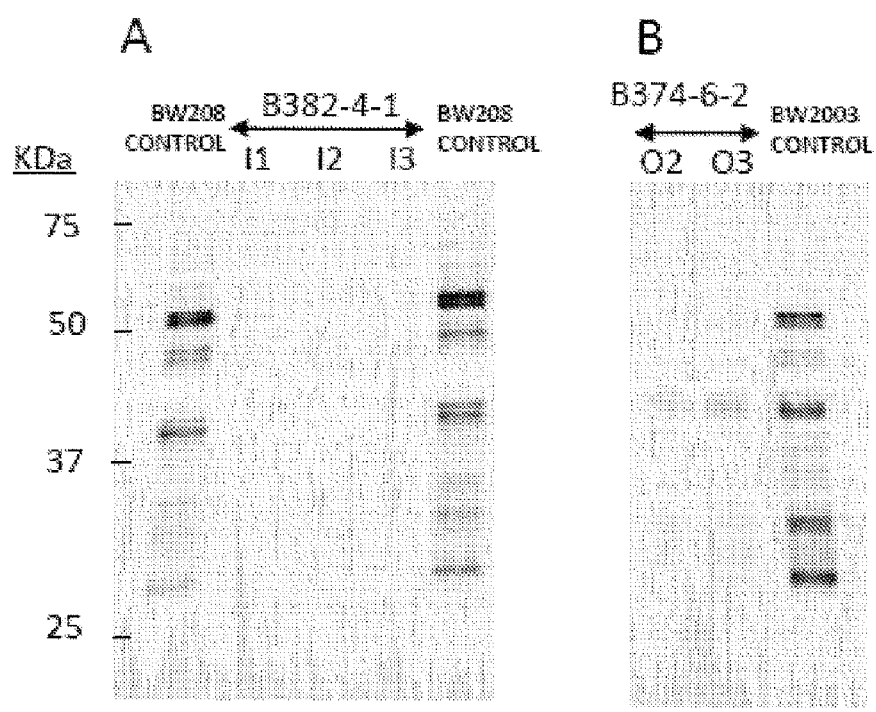

FIG. 7. Shows western blot analysis of two lines of wheat for flour (*Triticum aestivum* L.) transformed with the vector pDhp-ω/α/β/γ.

A: The gliadins of three grains of the line B382-4-1, denoted I1, I2, and I3, of the genotype BW208 were subjected to SDS gel separation and hybridized with the gluten-specific monoclonal antibody R5.

B: The gliadins of two grains of the line B374-6-2, denoted O2 and O3, of the genotype BW2003 were subjected to SDS gel separation and hybridized with the gluten-specific monoclonal antibody R5.

The numbers on the left in A indicate molecular weight in kDa, both for A and for B.

Figure 8:
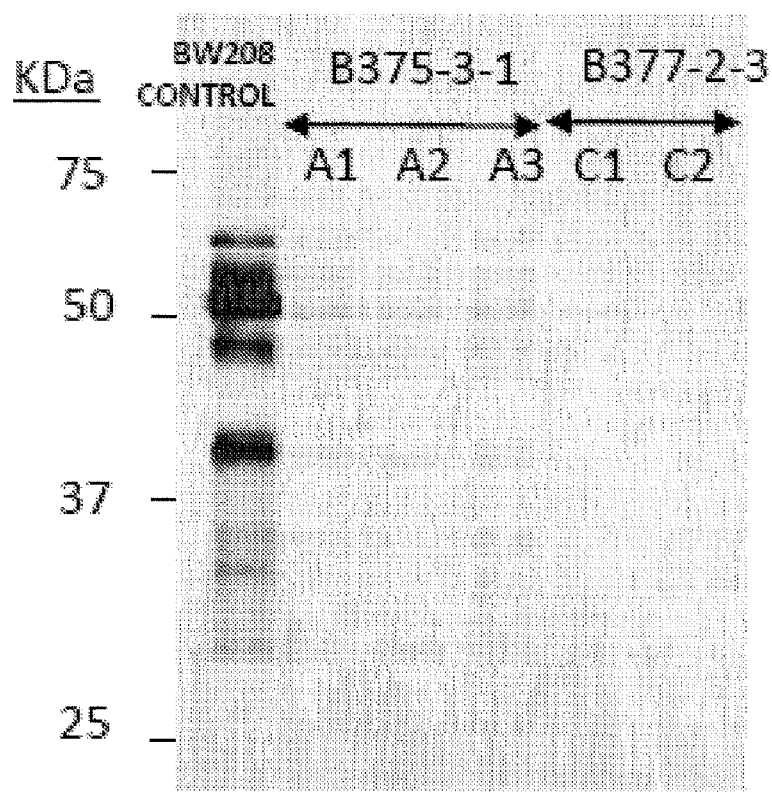

FIG. 8. Shows western blot analysis of two lines of wheat for flour (*Triticum aestivum* L.) of the variety BW208 transformed with the vector pGhp-ω/α/β/γ.

The gliadins of three grains of the transgenic line B375-3-1, denoted A1, A2, and A3, and the gliadins of two grains of wheat of the transgenic line B377-2-3, denoted C1 and C2, both of the genotype BW208, were subjected to SDS gel separation and hybridized with the gluten-specific monoclonal antibody R5.

The numbers on the left in the figure indicate molecular weight in kDa.

EXAMPLES

In the following, the invention will be illustrated by means of several tests conducted by the inventors that describe the construction of the polynucleotide of the invention, the generation of wheat plants of 3 distinct varieties transformed with the vector of the invention, and analysis of gliadin content using the techniques A-PAGE and MALDI-TOF.

Example 1

Construction of the Vectors pGhp-ω/α/β/γ and pDhp-ω/α/β/γ

1.1 Synthesis of α/β/γ and ω Gliadin Sequences

The DNA sequences deposited in the Genebank belonging to wheat α/β/γ and ω gliadins were aligned separately, and the regions showing the greatest degree of homology were identified. Based on these alignments, we selected a 170 bp sequence of α/β/γ gliadins and another 191 bp sequence of ω gliadins and designed the primers Alpha_hp-F (SEQ ID NO: 8) and Alpha_hp-R (SEQ ID NO: 9) for amplification of the α/β/γ fragment and the primers Omega_III-F (SEQ ID NO: 10) and Omega_III-R (SEQ ID NO: 11) for amplification of the ω fragment (Table 1). The PCR conditions for the two fragments were as follows: cDNA of *T. aestivum* cv Bobwhite synthesized from 50 ng of total RNA extracted from immature grains, 1.5 mM of $MgCl_2$, 0.2 mM of dNTPs, 0.2 μM of each primer, 1× buffer, and 0.625 units of a mixture of polymerases in a 100:1 ratio of Tth (*Thermus thermophilus*) to Pfu (*Pyrococcus furiosus*) (BIOTOOLS, Madrid, Spain) in a final reaction of 25 μl. The conditions of the PCR cycles were as follows: an initial pass of 94° C. 5 min, 35 cycles of 94° C. 30 sec, 55° C. 30 sec, and 72° C. 30 sec; and a final extension of 72° C. 4 min in a GeneAmp PCR system 9700 thermocycler (Applied Biosystems). The products of each PCR were purified using the GFX PCR DNA Purification Kit (Amersham Biosciences, Amersham, UK) and were sequenced by the firm Secugen SL. In order to achieve overlapping of the α/β and ω fragments, the ω gliadin fragment was again amplified using an overlapping primer (overlapping Omega III R (SEQ ID NO: 12) together with the direct primer SEQ ID NO: 10), and the α/β gliadin fragment was again amplified using another overlapping primer, overlapping Alpha F (SEQ ID NO: 13), together with the reverse primer SEQ ID NO: 9) which added to each fragment 12 base pairs that were complementary with the other fragment. By means of the latter amplifications, we obtained two fragments that complemented each other between the 3' end of the ω gliadin fragment and the 5' end of the α/β/γ gliadin fragment. The PCR conditions were the same as described previously; the product of these reactions was separated in 1% agarose gel and the band corresponding to each fragment was purified with the QUIAquick Gel Extraction Kit (QUIAGEN Inc., Valencia, Calif.). The final overlapping PCR was carried out using 10 ng of the α/β/γ purified overlapping fragment, 10 ng of the purified ω fragment, 1.5 mM of $MgCl_2$, 0.2 mM of dNTPs, 0.2 μM of the primer alpha_hp-F, 0.2 μM of the primer omega_III-R, 1× buffer, and 0.625 units of a 100:1 mixture of Tth/Pfu polymerases in a final reaction of 50 μl. The conditions of the PCR cycles were as follows: an initial pass of 94° C. 2 min, 35 cycles of 94° C. 30 sec, 57° C. 30 sec, and 72° C. 30 sec; and a final extension of 72° C. 4 min in a GeneAmp PCR system 9700 thermocycler (Applied Biosystems). The product of these PCR was separated in 1% agarose gel and the band showing the size corresponding to the ω/α/β (361 bp) fragment was purified with the QUIAquick Gel Extraction Kit (QUIAGEN Inc., Valencia, Calif.) and cloned in the plasmid TOPO (Invitrogen, Carlsbad, Calif.). This plasmid comprises the sites attL1 and attL2 that allow transference through recombination of the gene of interest into any Gateway® vector that comprises the sites attR1 and attR2.

1.2 Obtaining the Transformation Vectors pGhp-ω/α/β/γ and pDhp-ω/α/β/γ

The transformation vector was synthesized using the vector puc18 (2616 bp). The various fragments that comprise the transformation vector pGhp-ω/α/β/γ were introduced one by one into the multiple cloning site of the vector puc18. The fragment Nost (272 bp) was extracted from the vector pANDA-β by restriction with the enzyme EcoRI and introduced into the puc18, giving rise to puc18_Nost. Next, the fragment attRsense_GUS_attRantisense (4.4 kb) of the vector pANDA was extracted by restriction combined with the enzymes Sacl and Kpnl and introduced into the vector puc18_Nost, giving rise to puc18_attR_GUS_Nost. This fragment contained the sites attR1 and attR2 with sense and antisense sequences separated by a linking segment of 1 kb (gus linker). This gus linker sequence was substituted for the Ubi intron fragment (1019 bp) previously cloned in our laboratory by restriction with the enzyme EcoRV, producing the plasmid puc18_attR_Ubi_Nost. Finally the gliadin promoter (885 bp) was introduced by double restriction with the enzymes Sphl and Xhol, producing the plasmid puc18_Gli_attR_Ubi_Nost.

The D-hordein gene promoter (836 bp) was also introduced by double restriction with the enzymes SphI and XhoI, producing the vector puc18_D_attR_Ubi_Nost. The difference between the vectors pGhp-ω/α/β/γ and pDhp-ω/α/β/γ is that the former contains the promoter of wheat γ gliadins and the latter contains the promoter of wheat H-hordein.

The next step was the introduction of the fragment ω/α/β into the plasmids puc18_Gli_attR_Ubi_Nost and puc18_D_attR_Ubi_Nost. The plasmid TOPO+ ω/α/β contained the sites attL1 and attL2, while the plasmids puc18_Gli_attR_Ubi_NOSt and puc18_D_attR_Ubi_Nost contained the sites attR1 and attR2 with sense and antisense sequences separated by the intron Ubi. This made it possible to carry out an LR recombination reaction using the kit Gateway® LR Clonase™ Enzyme Mix (Invitrogen, Carlsbad, Calif.) and following the manufacturer's instructions. The result was the introduction of the fragment ω/α/β/γ having sense and antisense sequences separated by the intron Ubi into the structure of the plasmids puc18_Gli_attR_Ubi_NOSt and puc18_D_attR_Ubi_Nost. The resulting vectors were designated pGhp-ω/α/β/γ and pDhp-ω/α/β/γ (FIG. 2) and were introduced by transformation into competent $E.\ coli$ cells (DH5α) for their subsequent multiplication.

Example 2

Obtaining Transgenic Wheat Lines

Genetic transformation was carried out by biolistics using a system for accelerating particles with pressurized helium (PDS1000/He™. BIORAD, Hercules, Calif.). We used two genotypes of wheat for flour (Triticum aestivum L.) cultivar Bobwhite (BW208 and BW2003) and one of hard wheat (Triticum turgidum ssp durum) cultivar Don Pedro to isolate the scutella of immature embryos. Isolation was carried out in a sterile environment using immature wheat grains collected 12-16 days after anthesis, previously sterilized by immersion for 3 min in a 70% ethanol solution, 10 min in a 20% sodium hypochlorite solution, and rinsing twice with sterile distilled $H_2O$. For genetic transformation, we used gold particles 0.6 μm in diameter and mixed in 1.5 pmoles/mg gold of the vector pGhp-ω/α/β/γ or the vector pDhp-ω/α/β/γ and 0.5 pmoles/mg of the vector pAHC25 (Christensen et al., 1996. Transgenic Research 5, 213-218). The conditions of each shot were as follows: 91.4 kPa (27 inHg) vacuum pressure, 7.584 MPa (1100 PSI) shot pressure, 6 cm shot distance, and 60 μg of the mixture of gold and plasmids per shot.

Cotransformation with the plasmid pAHC25, which contains the bar selection gene (resistance to phosphinothricin) and the uidA gene (synthesis of β-glucuronidase), allowed selection of the tissues transformed in media with 4 mg/l of phosphinothricin (PPT) and subsequent identification of transgenic tissues by means of the β-glucuronidase assay (GUS) in accordance with the protocol described by Jefferson (1987, Plant Mol Biol Rep 5:387-405). The media, the in vitro cultivation process, and regeneration of the plants were in accordance with Barro et al (Barro et al., 1998. Theoretical and Applied Genetics 97, 684-695).

The plants regenerated in in vitro cultivation were placed in the soil, and they were then subjected to the GUS assay per se and as described in the previous paragraph. From the plants that yielded a positive result in the GUS assay, DNA was extracted using DNAzol reagent (Invitrogen, Carlsbad, Calif.) following the manufacturer's instructions, and PCR was carried out to confirm the presence of the plasmids pGhp-ω/α/β/γ, pDhp-ω/α/β/γ, and pAHC25 in the genome of the adult plant. PCR conditions were as follows: 100 ng of DNA extracted from young leaves, 1.5 mM $MgCl_2$, 0.2 mM dNTPs, 0.2 μM of each primer, 1× buffer, and 0.625 units of polymerase Tth (BIOTOOLS, Madrid, Spain). The primers used were prGliF (SEQ ID NO: 14) and overlapping Omega_III_R (SEQ ID NO: 12) for the plasmid pGhp-ω/α/β/γ, prHorDF (SEQ ID NO: 15) and overlapping Omega_III_R (SEQ ID NO: 12) for the plasmid pDhp-ω/α/β/γ and BAR_F (SEQ ID NO: 16) and BAR_R (SEQ ID NO: 17) for pAHC25 (Table 3). The conditions of the PCR cycles were as follows: an initial pass of 94° C. 5 min, 35 cycles of 94° C. 30 sec, 55° C. 30 sec, and 72° C. 2 sec; and a final extension of 72° C. 7 min in a GeneAmp PCR system 9700 thermocycler (Applied Biosystems). The product of each PCR was separated by electrophoresis in 1% agarose gel, and the positive lines were selected for subsequent analysis.

TABLE 3

Primers and sequences used.

| Primer | 5' to 3' sequence |
| --- | --- |
| Alpha_hp_F | (SEQ ID NO: 8) |
| Alpha_hp_R | (SEQ ID NO: 9) |
| Omega_III_F | (SEQ ID NO: 10) |
| Omega_III_R | (SEQ ID NO: 11) |
| Overlapping Omega_III_R | (SEQ ID NO: 12) |
| Overlapping Alpha_F | (SEQ ID NO: 13) |
| prGli_F | (SEQ ID NO: 14) |
| prHorDF | (SEQ ID NO: 15) |
| BAR_F | (SEQ ID NO: 16) |
| BAR_R | (SEQ ID NO: 17) |

Example 2

Extraction of Gliadins and MALDI/TOF and A-PAGE Analysis

The seeds of the positive lines were crushed in a mortar to obtain flour. After this, the flour was washed with 1 ml of a 0.5 M NaCl solution for 15 minutes at room temperature (RT) in an agitator and centrifuged at 13,000 rpm for 10 min. The supernatant was discarded, and the precipitate was washed with distilled water for 15 min at RT, also under agitation. After this, the samples were centrifuged at 13,000 rpm for 10 min, after which the supernatant was discarded. The gliadins were extracted from the precipitate with 60% (v/v) aqueous ethanol solution in a 5:1 ratio (μl ethanol:mg flour) and agitation was carried out for 45 min at RT. The samples were then centrifuged at 13,000 rpm and the supernatant containing the gliadins was collected in fresh tubes. A fraction of the extract was used for identification of the gliadins by MALDI-TOF mass spectrometry, and another fraction was separated by acidic polyacrylamide gel electrophoresis (A-PAGE). For the MALDI analysis, we took 5 μl of the gliadin extracted and added to this 2 μl of a 50 mM octyl-β-D-glucopyranoside (ODGP) solution and 25 μl of sinapic acid saturated in a 30% (v/v) aqueous acetonitrile solution containing 0.1% (v/v) of trifluoroacetic acid (TFA), used as a matrix solution. The mixture was dried in a Speed-Vac centrifuge for 15 min, and the residue was dissolved in 6 μl of a 60% (v/v) aqueous ethanol solution containing 0.1% TFA. The mixture was placed in a stainless steel sample holder and allowed to dry for 5 min at RT. The samples were analyzed in a MALDI-TOF Voyager DE-PRO (PE Biosystems) in the standard instrument configuration. Spectra were recorded in linear positive mode at a voltage acceleration of 25 kV with a voltage grid of 93% and a delay of 700 nanoseconds. 200 laser spectra were accumulated to construct the gliadin profiles.

The gliadins were subjected to gel separation by A-PAGE following the standard protocols described by Khan et al. (1985. *Cereal Chemistry* 62: 310-313).

Hybridization (western blot) of the gliadins subjected to gel separation by SDS-PAGE was carried out with the antibody R5 (Valdez et al. 2003, *Eur. J. Gastroenterol. Hepatol.* 15:465-474), as this is the official method recognized by the Codex Alimentarius for the detection of gluten in food.

The A-PAGE and MALDI-TOF gel assays showed that the combination of this hybrid sequence is highly effective in silencing wheat gliadins.

FIG. 3 shows separation and identification of gliadins of plant seeds of the wheat cultivar BW208 transformed with the polynucleotide of the invention by means of the A-PAGE and MALDI-TOF techniques. In FIG. 3A, one observes band attenuations corresponding to each of the alpha, beta, gamma, and omega gliadins derived from seeds of a line of wheat for flour transformed with the vector pGhp-ω/α/β/γ (B377-2-3) compared to the wheat cultivar BW208 from which it is derived (*Triticum aestivum* L. ssp. *aestivum*). In FIG. 3B, one observes the spectral expression profile corresponding to the alpha, beta, gamma, and omega gliadins, with each of the peaks corresponding to a different protein. In the diagram, the peaks corresponding to each type of gliadin are indicated. As can be observed in the expression profiles corresponding to the control plants and those of the plants transformed with the polynucleotide of the invention, the suppression of the peaks corresponding to each of the gliadins observed in the profile of the control plants is quite distinct, thus demonstrating the efficacy of the polynucleotide and method of the present invention in post-transcriptional silencing of the gliadins present in the grains of wheat belonging to this cultivar.

FIGS. 4 and 5 show the separation and identification of gliadins of plant seeds of the wheat cultivar BW2003 (*Triticum aestivum* L. ssp. *aestivum*) and the variety Don Pedro (*Triticum turgidum* L. ssp *durum*) respectively transformed with the polynucleotide of the invention by means of the A-PAGE technique. In both cases, one can see the band attenuation corresponding to each of the alpha, beta, gamma, and omega gliadins derived from seeds of the wheat lines transformed with the vector pGhp-ω/α/β/γ (B377-2-3) compared to their respective controls.

FIG. 6 shows A-PAGE gliadin gel separation of a control line BW208 and three seeds of a line (B382-4-1) of the same genotype transformed with the vector pDhp-ω/α/β/γ. The promoter that contains this vector is the promoter of a gene D-hordein (SEQ ID NO: 7). One can see the band attenuation in the seeds of the transgenic lines corresponding to each of the alpha, beta, gamma, and omega gliadins of wheat.

FIG. 7 shows a western blot analysis of two lines of wheat for flour (*Triticum aestivum* L. ssp. *aestivum*) transformed with the vector pDhp-ω/α/β/γ that contain the promoter coded for by the sequence SEQ ID NO: 7.

In gel A, one can see the SDS-PAGE gel separation of the gliadins of three wheat grains (|1, |2, and |3) of the transgenic line B382-4-1. In gel B, one can see the separation of the gliadins of two wheat grains (O2 and O3) of the transgenic line B374-6-2. After this, both gels underwent hybridization with the monoclonal antibody R5, which recognizes peptides that are potentially toxic for celiac patients. Monoclonal antibody R5 is the method officially recognized by the Codex Alimentarius for the detection of gluten in food.

In FIG. 7A, one does not observe an appreciable level of gliadins in the BW208 wheat lines that express the peptide of the invention, which is expected for this type of detection with the antibody R5. In FIG. 7B, one can see a considerable reduction of gliadins in this other transgenic wheat variety BW2003.

In FIG. 8, one sees on an SDS-PAGE gel the attenuation of the gliadins of the three grains of the transgenic line B375-3-1, designated A1, A2, A3, and the gliadins of the two wheat grains of the transgenic line B377-2-3, both of the genotype BW208, when they hybridize with the R5 gluten-specific antibodies. The transgenic lines contain the promoter of γ gliadins, i.e., they are transformed with the vector pGhp-ω/α/β/γ.

The invention claimed is:

1. A polynucleotide comprising two sequence pairs (a1-a2) and (b2-b1) separated by a spacer sequence wherein:
   (a) the sequences a1, a2, b1, and b2 differ among themselves and are selected from the group consisting of SEQ ID NO: 1, SEQ ID NO: 2, SEQ ID NO: 3, and SEQ ID NO: 4;
   (b) if a1 is SEQ ID NO: 1 or SEQ ID NO: 4, then b1 is SEQ ID NO: 4 or SEQ ID NO: 1, a2 is SEQ ID NO: 2 or SEQ ID NO: 3, and b2 is SEQ ID NO: 3 or SEQ ID NO: 2; and
   (c) if a1 is SEQ ID NO: 2 or SEQ ID NO: 3, then b1 is SEQ ID NO: 3 or SEQ ID NO: 2, a2 is SEQ ID NO: 1 or SEQ ID NO: 4, and b2 is SEQ ID NO: 4 or SEQ ID NO: 1.

2. The polynucleotide of claim 1, wherein the polynucleotide comprises two sequence pairs (a1-a2) and two sequence pairs (b2-b1).

3. The polynucleotide of claim 1, wherein a1 is SEQ ID NO: 1, a2 is SEQ ID NO: 2, b2 is SEQ ID NO: 3, and b1 is SEQ ID NO: 4.

4. The polynucleotide of claim 1, wherein the spacer sequence is SEQ ID NO: 5.

5. The polynucleotide of claim 1, further comprising a gene expression-regulating sequence functionally linked to the 5' end of the polynucleotide.

6. The polynucleotide of claim 5, wherein the gene expression-regulating sequence is SEQ ID NO: 6 and/or SEQ ID NO: 7.

7. An RNA sequence encoded by the polynucleotide of claim 1, wherein the RNA sequence forms an hpRNA in which the sequence coded for by the pair a1-a2 completely hybridizes with the sequence coded for by the pair b2-b1.

8. An expression vector comprising the polynucleotide of claim 1.

9. An isolated cell transfected with the expression vector of claim 8.

10. A genetically modified plant that comprises the isolated cell of claim 9.

11. The plant of claim 10, wherein the plant belongs to the genus *Triticum*.

12. The plant of claim 11, wherein the plant belongs to the species *Triticum aestivum* or *Triticum turgidum*.

13. The plant of claim 12, wherein the plant is a Bobwhite cultivar or a Don Pedro cultivar.

14. A seed of the plant of claim 10 wherein the seed comprises the expression vector.

15. A pollen, propagule, progeny, or part of the plant of claim 10 wherein said pollen, propagule, progeny, or part of the plant comprises said expression vector.

16. A method for silencing the alpha, beta, gamma, and omega gliadins of *Triticum* spp, the method comprising providing a plant of the genus *Triticum* and administering to the plant a polynucleotide of claim 1.

17. A method for obtaining a genetically modified plant, the method comprising the following steps:
   (a) selecting a part of a plant,
   (b) transfecting cells of the part of the plant with the vector of claim 8, thereby producing a transfected cell,
   (c) selecting the transfected cell,
   (d) regenerating at least one plant derived from the transfected cell,
   (e) selecting one or more plants derived from the transfected cell, and
   (f) selecting one or more plants obtained according to paragraph (e) that show silencing of the alpha, beta, gamma, and omega gliadins in its seeds.

18. A genetically modified plant comprising the polynucleotide of claim 1, wherein the polynucleotide is integrated into the plant's genome and the plant has a reduced gliadin content relative to a control plant.

19. A method of producing a genetically modified plant that has a reduced gliadin content, the method comprising integrating the polynucleotide of claim 1 into the genome of the plant, wherein expression of the polynucleotide silences alpha, beta, gamma, and omega gliadins in seeds of the plant and thereby reduces gliadin content in the plant.

* * * * *